US008690813B2

(12) United States Patent
Thompson

(10) Patent No.: US 8,690,813 B2
(45) Date of Patent: Apr. 8, 2014

(54) RADIATION TREATMENT GARMENT—I

(76) Inventor: Elizabeth Chabner Thompson, Scarsdale, NY (US)

( * ) Notice: Subject to any disclaimer, the term of this patent is extended or adjusted under 35 U.S.C. 154(b) by 247 days.

(21) Appl. No.: 13/336,198

(22) Filed: Dec. 23, 2011

(65) Prior Publication Data

US 2013/0019874 A1 Jan. 24, 2013

Related U.S. Application Data

(60) Provisional application No. 61/510,849, filed on Jul. 22, 2011.

(51) Int. Cl.
*A61F 13/06* (2006.01)

(52) U.S. Cl.
USPC .......... 602/61

(58) Field of Classification Search
USPC .......... 602/60, 61, 67–73, 19; 128/845, 849, 128/856, 854, 869, 870, 873, 874
See application file for complete search history.

(56) References Cited

U.S. PATENT DOCUMENTS

| | | | |
|---|---|---|---|
| 3,511,234 A * | 5/1970 | Larson | 602/67 |
| 4,378,010 A | 3/1983 | McDonald | |
| 4,557,260 A | 12/1985 | Reyes, Jr. | |
| 5,131,386 A | 7/1992 | Simmons | |
| 5,295,945 A | 3/1994 | Miller | |
| 5,343,876 A | 9/1994 | Rogers | |
| 5,595,191 A | 1/1997 | Kirk | |
| 6,493,417 B1 | 12/2002 | Baer et al. | |
| 7,211,814 B2 | 5/2007 | Cadwalader et al. | |
| 7,438,685 B2 | 10/2008 | Burdette et al. | |
| 7,853,311 B1 * | 12/2010 | Webb | 600/426 |
| 8,007,457 B2 | 8/2011 | Taylor | |
| 8,376,977 B2 * | 2/2013 | Farrow et al. | 602/60 |
| 2002/0023652 A1 | 2/2002 | Riaziat et al. | |
| 2005/0213712 A1 | 9/2005 | Cadwalader et al. | |
| 2007/0074347 A1 | 4/2007 | Coppens et al. | |
| 2008/0040831 A1 | 2/2008 | Nilforushan | |
| 2008/0119722 A1 | 5/2008 | Swaney | |
| 2009/0129556 A1 | 5/2009 | Ahn | |
| 2009/0171259 A1 * | 7/2009 | Soerensen et al. | 602/67 |
| 2009/0178182 A1 * | 7/2009 | Dahlquist | 2/401 |
| 2010/0237259 A1 | 9/2010 | Wang | |
| 2012/0024296 A1 * | 2/2012 | Long Sharps et al. | 128/845 |
| 2012/0253256 A1 * | 10/2012 | Dahlquist | 602/67 |

FOREIGN PATENT DOCUMENTS

JP 2006225810 A 8/2006

* cited by examiner

*Primary Examiner* — Patricia Bianco
*Assistant Examiner* — Raymond E Harris
(74) *Attorney, Agent, or Firm* — Kaplan Breyer Schwarz & Ottesen, LLP

(57) ABSTRACT

A radiation treatment garment includes, in some embodiments, a window having a visually-transparent material for viewing alignment tattoos on a wearer. In some other embodiments, the radiation treatment garment includes a support pouch for receiving and supporting a male wearer's external genitalia, wherein the support pouch is configured to support the external genitalia in a position that is anterior and superior to the natural gravity-induced position. In some further embodiments, the radiation treatment garment includes both the window and the support pouch.

24 Claims, 6 Drawing Sheets

FIG. 1D
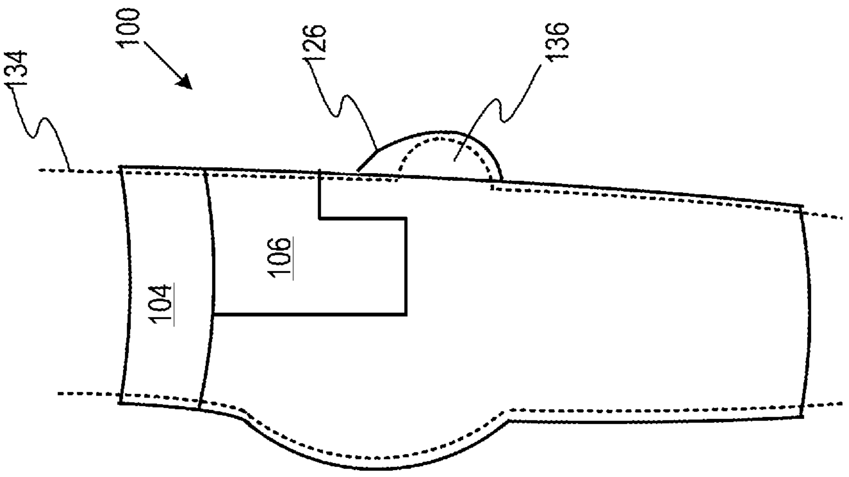
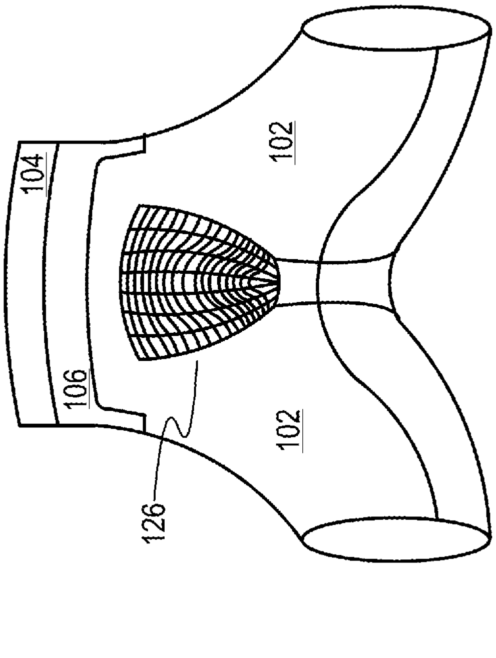
FIG. 1C

RADIATION TREATMENT GARMENT—I

STATEMENT OF RELATED CASES

This case claims priority to U.S. Provisional Patent Application 61/510,849, filed Jul. 22, 2011, which is incorporated by reference herein.

FIELD OF THE INVENTION

The present invention relates to radiation oncology in general and, more particularly, to a garment for use during an abdominal or pelvic radiation treatment session.

BACKGROUND OF THE INVENTION

Radiation therapy is often indicated for dozens of types of cancer in the abdomen and pelvic region of both men and women. Targets often include organs with cancer involvement and lymph node chains. For example, in 2011, approximately 300,000 men will develop cancers which necessitate radiation treatment to the abdomen, retroperitoneal and pelvic areas. For men with prostate and anal cancer, radiation therapy is often primary and curative. For others with prostate cancer who are not surgical candidates, or who have bladder or anal cancers or sarcomas involving the pelvis, radiation therapy is standard treatment with either a curative or palliative intent. For women, numerous cancers involving the abdomen, retroperitoneal and pelvic organs can be treated both with curative and palliative intention.

The course of radiation treatment for such cancers usually continues for a minimum of three weeks up to as much as seven weeks of daily therapy. The radiation is intended to kill tumor cells and spare normal surrounding tissue. Treatment is often done with 3-dimensional conformation or in an intensity-modulated or intensity-graded fashion to deliver maximal dose to the intended target and minimal radiation to the normal surrounding tissue. A specialist physician (i.e., radiation oncologist) works in conjunction with a team of physicists, dosimetrists, and radiation-therapy-machine operators ("therapists") to plan and deliver the radiation treatment.

Since multiple radiation treatment sessions are required, a reproducible set-up is necessary to ensure that the target site receives the intended cumulative dose of radiation while the surrounding normal tissue is spared. This frequently involves permanent tattoo placement on the patient's skin so that the patient is lined up without rotation and each treatment can be precisely reproduced from the treatment plan. The tattoos enable precise set-up via laser triangulation; the tattoos must therefore be visible at each treatment session so that they can be aligned with a light field projected by the treatment apparatus. Furthermore, the precise height and table position depends upon shining a light field on the patient's skin and matching measurements and parameters made during treatment planning. In this way, through tattoo alignment for patient position and light field visualization for table height and rotation, the exact position can be reproduced each treatment. In conjunction with IMRT and IGRT and the CT scan, precise treatment may be delivered. In order to ensure tattoo and light-field visualiztion, patients are therefore traditionally treated without clothing or coverage of their genitalia. This is a source of some (psychological) discomfort and an indignity for many patients.

While the target volume for radiation therapy is often deep within the pelvis, the skin of the perineum and external genitalia often receives some unavoidable radiation dose. It is well recognized that acute and late morbidity can be reduced with careful planning and by limiting the amount of unintended irradiation received by the sensitive skin of the perineum and external genitalia. Fractionated doses delivered over the course of weeks are often recommended; daily fractions of less than 2 Gy are typical.

The curvatures, folds and irregularities of the perineum, scrotum, and labia can often lead to higher than desirable skin dose. Variations up to 10% can be seen in the dose to the skin redundancy. Accurate radiation values at the skin-air interfaces are extremely difficult to predict even with CT planning. As a result, male patients can receive higher doses than desired to the skin of the abdomen, perineum and scrotum simply because of male anatomy and the traditional treatment of men in a supine position without clothing or gown/sheet covering. The same is true for women receiving treatment to the abdomen, pelvic, and retroperitoneal areas.

Furthermore, the dry and moist desquamation (i.e., raw, peeling areas of skin) that can develop in hotspots and in areas where tissue folds upon itself can necessitate treatment breaks until the skin recovers. These treatment breaks compromise the efficacy of the radiation in killing cancer cells.

The optimal radiation therapy outcomes are achieved when (a) precise radiation treatment parameters are followed, (b) reproducible set-up is established and (c) patients are able to complete the scheduled treatment prescription without treatment breaks from acute skin toxicity. Receiving the full cumulative dose reduces the patient's risk of developing a local recurrence of the cancer or metastatic spread of the disease.

The prior art has proposed a variety of ways to address these and other problems associated with radiation treatment. For example, there have been a number of proposals for minimizing the radiation exposure of healthy tissues surrounding the target (e.g., prostate, etc.).

U.S. Publ. Pat. Appl. 2002/0023652, for instance, discloses a system and method for measuring and correcting the position of a patient with respect to a radiation treatment apparatus. According to this reference, reference coordinates at various locations on a patient's body are measured and stored. Prior to treatment, the patient must be positioned so that the actual coordinates of these locations on the patient's body match the reference coordinates. To achieve this, the patient is placed on a treatment table. The patient is likely to be out of position relative to the reference coordinates. The process begins by correcting a patient's posture, which refers to the position of one or more of the patient's body parts relative to that patient's other body parts. This is done by repositioning the measured body locations of the patient to match the relative positioning of the reference coordinates. Once the posture has been corrected, the measured body locations will be correct with respect to the rest of the patient's body. But the absolute coordinates of the body positions might be incorrect with respect to the treatment machine. As long as the posture is correct, all body locations will be misaligned by the same offset when compared to the reference values. The patient's entire body is then shifted as a single unit to place the patient in the correct absolute coordinates that match the reference coordinates.

U.S. Pat. No. 7,438,685 discloses an apparatus and method for registration, guidance and targeting of external beam radiation therapy. According to this reference, real-time ultrasound imaging during planning and treatment is used to localize soft tissue treatment targets and is fused with radiographic or CT data for conformal treatment optimization. This fusion technique supposedly provides accurate localization of the prostate or other target volume in real time. With an unambiguous localization of the target tissue, the radiation field can be optimized to reduce the volume of normal tissue that is irradiated.

U.S. Publ. Pat. Appl. 2010/0237259 discloses a method and device for image-guided dynamic radiation treatment. According to this reference, high doses of radiation can be administered to prostrate while sparing surrounding healthy tissue using a collimation method and apparatus that sculpts the radiation borders. The system/approach incorporates radiation sources that use a "fan" geometry, a collimation apparatus, an integrated 3d imager and tissue-interface imaging system to locate and track critical boundaries in real time, a dynamic patient support system that is shared by the imager and irradiation system, and motorized shielding filters.

As previously noted, another issue related to radiation treatment is the fact that the patient is often naked during planning and treatment sessions. JP 2006225810 (A) addresses this problem with a radiation therapy garment. The garment includes openings (32) and (22) that can be covered with closures. These openings permit treatment personnel to establish alignment, such as by aligning laser beams with alignment tattoos (M2) and (M3) shown in FIG. 3. Furthermore, the patient can be treated at M1 with a treatment beam through larger opening (22). Although the openings must be open for alignment and treatment, the garment does provide the patient with a modicum of privacy. The garment is loose fitting and does not provide any functionality other than simply "coverage" of the patient.

SUMMARY OF THE INVENTION

The present invention provides a way to improve radiation-treatment outcomes and provide an improved experience for the patient. In particular, embodiments of the present invention provide any one or more of the following benefits:

i. decreased exposure of healthy tissue to radiation;

ii. improved homogeneity of radiation distribution to body tissues; and iii. enhanced privacy for the patient.

The illustrative embodiment of the invention is a radiation treatment garment that is worn during a radiation treatment session and can be worn during radiation planning sessions, as well. In some embodiments, the garment is in the form of a pair of "shorts." In some other embodiments, which are particularly suitable for use by women, the garment is the form of a shapewear-style "girdle." The garment can be worn for use with all treatment machines without causing bolus effect. The garment is undetectable during CT scan and water phantom dosimetry testing.

The shorts are intended for, but not restricted to use by, men. The shorts are advantageously configured from a compression fabric as used in athletic-style "compression" shorts.

For men, the shorts include a "support pouch" that receives the male external genitalia. The support pouch comprises a non-compression fabric, such as cotton. A sufficient amount of non-compression fabric is present so that the material forms a forwardly projecting but supported "pouch." The pouch is configured to receive the male external genitalia and maintain it in a "forward" (anterior) and "up" (superior) position, against gravity. The compressive nature of the fabric immediately surrounding the pouch tends to "direct" the external genitalia into the pouch.

For a patient being treated by radiation therapy for prostate or anal cancer, for example, maintaining the external genitalia in an anterior and superior position via the support pouch significantly reduces the amount of radiation the genitalia would otherwise be exposed to. Supporting the external genitalia in this position also simplifies radiation planning.

In some embodiments, the shorts include an anterior, laterally-extending window. The window, which may be a single window or multiple windows, enables the physician and therapist to view the midline and treatment parameters and tattoos, as created in the light field that is projected by the treatment machine onto the patient's pelvic area. Thus, a patient wearing the shorts can be aligned to the treatment machine.

As previously indicated, in some embodiments, a radiation treatment garment in accordance with the present invention is configured as a girdle. The girdle configuration is intended for, but not restricted to use by, women. The girdle comprises a compression material like the shorts.

The girdle includes a window, which extends vertically along the midline of the girdle. In some embodiments, the girdle comprises a "bottom," such that the girdle covers the pelvic area of the patient, akin to a one-piece bathing suit (but without the "bra" portion). In such embodiments, in addition to extending in a vertical direction along the midline of the girdle, the window (or another window or windows) extends laterally below the naval, such that the window(s) defines a shape similar to an upside-down "T".

It is important for all radiation treatment garments disclosed herein that the window(s) are not simply "openings." Rather, the window(s) must be "covered" openings; covered with a visually-transparent material. A transparent covering is required because the radiation treatment garments disclosed herein are intended to fit quite snugly. The purpose for the snug fit is to reduce, control, or otherwise smooth the skin/tissue to prevent folds, etc., that naturally occur when a patient is lying in the supine position or simply because of an individual's habitus. As noted in the "Background" section, these folds, etc., can cause a variety of problems (e.g., non-homogenous distribution of radiation, dry and moist desquamation, etc.). If the windows were simply openings, then a patient's skin, particularly in the case of an overweight/obese person, would tend to protrude from these openings, causing the problems referenced above.

In embodiments in which the window is formed from suitable material, alignment tattoos can be created through the windows themselves, such that the shorts can be worn during radiation planning sessions.

And no less important than the aforementioned functions, embodiments of the radiation treatment garment provide privacy and dignity for the patient in a way not available until now.

BRIEF DESCRIPTION OF THE DRAWINGS

FIG. 1C depicts a further view of the radiation treatment garment of FIG. 1A, showing the contours of a support pouch of the garment.

FIG. 1D depicts a further detail of the radiation treatment garment of FIG. 1A, showing the relationship between the garment and portions of the male anatomy.

DETAILED DESCRIPTION

Figure 1A:
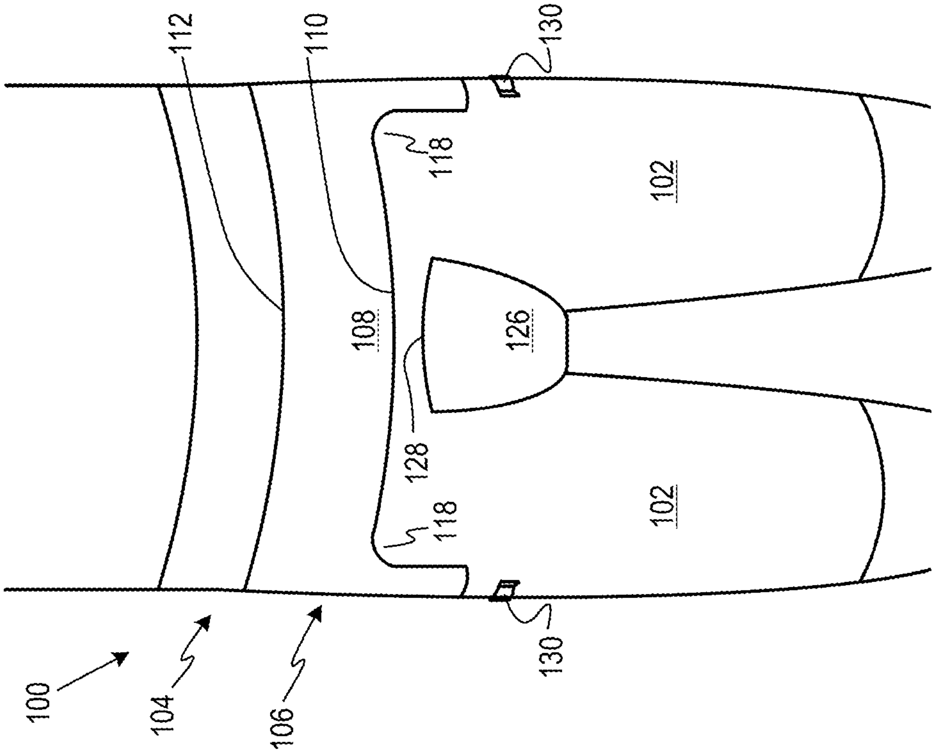
FIG. 1A depicts a front view of a first embodiment of a radiation treatment garment in accordance the present invention.
Figure 1B:
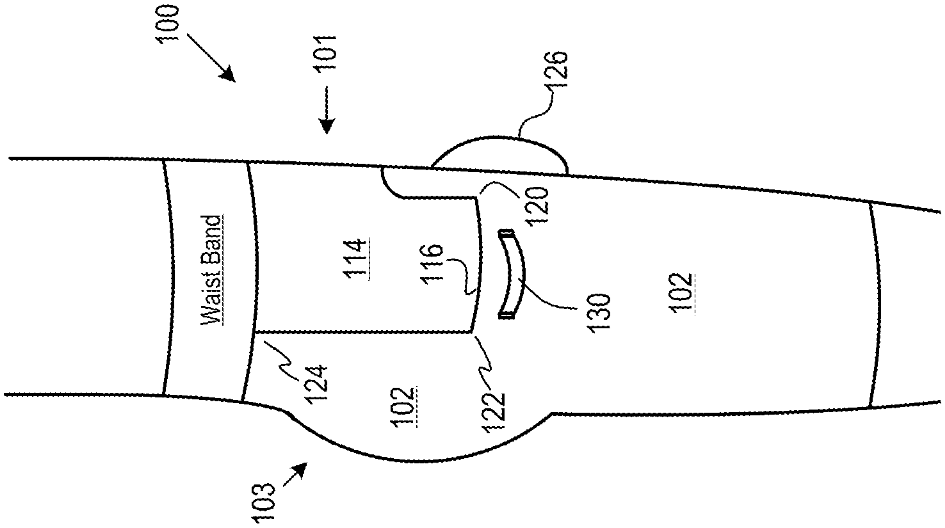
FIG. 1B depicts a side view of the radiation treatment garment of FIG. 1A.

FIGS. 1A and 1B depict respective front and side views of radiation treatment garment 100 in accordance with a first illustrative embodiment of the present invention. Garment 100 is in the form of a pair of "shorts."

Garment 100 includes front portion 101, leg portions 102, back portion 103, and waist band 104.

Much of garment 100, including back portion 103, most of leg portions 102, and some of front portion 101 comprises a fabric that is resilient and elastic, such as a spandex-type fabric (e.g., as used in "compression" shorts, cycling shorts, etc.). The term "compression fabric" is hereinafter used in this disclosure and the appended claims to refer to this spandex-type fabric. An example of a suitable compression fabric is spandex "tricot," in a matte or other finish, having a composition of about 15%-20% spandex and 85%-80% nylon. Other compositions and materials may suitably be used. Matte tricot is available from Darlington Fabrics Corporation and others. It is important that the compression fabric selected, which is the primary constituent of garment 100, will not scatter or otherwise substantially attenuate the radiation treatment beam or add bolus effect.

Waist band 104 encircles the waist opening of garment 100 near the superior edge thereof and is intended to keep the garment snug to the wearer. As discussed further below, waist band 104 must not obscure any alignment tattoos or markings. Those markings are usually at the level of the wearer's iliac crest. As such, locating waistband 104 such that it is no lower than about 5 to 8 centimeters below the umbilicus of the wearer is acceptable.

In the illustrative embodiment, waist band 104 comprises an elastic material, such as a fabric comprising 90% nylon and 10% spandex, as is available from Stretchline (UK). Other compositions and materials may suitably be used. In some alternative embodiments, a discrete waist band is not provided since the compression fabric from which garment 100 is made is suitable for keeping it snug to a wearer's waist.

Garment 100 also includes window 106. This window enables a light field, which originates from the radiation treatment machine, to be projected onto a patient wearing garment 100 and viewed. During a radiation planning session, using the light field as a guide, temporary and then permanent marks (i.e., tattoos) are placed on the patient to establish the requisite alignment with respect to the treatment machine. The tattoos are placed at about the level of the patient's iliac crest. The tattoos are later used to re-establish the requisite alignment for actual radiation treatment sessions.

In the embodiment depicted in FIGS. 1A/1B, window 106 extends fully across front 101 of the shorts, terminating at approximately the mid-point of the sides of the shorts, at lateral window portions 114. Upper edge 112 of anterior portion 108 of window 106 is disposed adjacent to and below to waist band 104. Lower edge 110 of anterior portion 108 of window 106 is proximal to the wearer's pubic symphysis and just above top 128 of support pouch 126.

By way of example, in some embodiments, the inferior edge of anterior portion 108 of the window is no more than about 5 centimeters superior to the wearer's pubic symphysis. In some other embodiments, the inferior edge of anterior portion 108 of the window is no more than about 7.5 centimeters superior to the wearer's pubic symphysis. The significance of this placement is to ensure that all alignment tattoos on the wearer in the region of the pelvis are visible. It will be appreciated that there is a normal variation in pelvis size from individual to individual. As a consequence of that anatomical variation, and further in view of the expected variation in the fit of garment 100 (in an appropriate size) on a given individual, the optimum location of the window on a given garment 100 will vary. As such the aforementioned distances should be considered to be working guidelines. What is important is that the location of the window (on the garment) is such that when the garment is worn, any alignment tattoos/marks on the wearer in the region of the pelvis are visible through the window. In a treatment setting, garment 100 will be available in a number of sizes such that a clinician can individually fit a patient with an appropriately-sized version of garment 100 to achieve the stated goal.

Window 106 also includes lateral portion 114. Lower edge 116 of lateral portion 114 of window 106 is inferior (i.e., extends further down leg portions 102) than lower edge 110 of anterior portion 108 of the window.

Window 106 is not simply an opening in the compression fabric. Rather, it comprises a clear/visually transparent material that is free of metals or other constituents that will scatter or substantially attenuate a radiation treatment beam or cause bolus effect. In some embodiments, window 106 comprises a clear thermoplastic material, such as Clear-Fit TPU brand thermoplastic polyurethane, commercially available from Fulflex, Inc. of Brattleboro, Vt. When the material used for window 106 is made from Clear-Fit TPU brand thermoplastic polyurethane or other suitably selected materials, the alignment tattoos can be made through the window without damaging the window or compromising the alignment.

With continuing reference to FIGS. 1A and 1B, and now also referring to FIGS. 1C and 1D, support pouch 126 is located in front 101 of garment 100 below window 106 and proximal to the external male genitalia. There is an opening (not depicted) in the compression fabric at this location; support pouch 126 covers the opening. The support pouch is intended to receive and support the male external genitalia.

In the illustrative embodiment, support pouch 126 comprises a fabric that is not compressive or is at most minimally compressive, such as, for example, a cotton knit fabric. A sufficient amount of fabric is provided so as to provide a volume suitable for receiving the external male genitalia and causing that the genitalia-containing support pouch to project in an anterior direction with respect to the rest of the shorts. Entry of the external male genitalia into support pouch 126 is facilitated by: (1) the presence of compression fabric surrounding support pouch 126; (2) the ample amount of fabric defining the support pouch, and (3) the non/minally compressive character of the fabric used for the pouch. As used hereinafter, the term "non-compression fabric" refers to a fabric, which, either due to the nature of the fibers thereof or the manner in they are arranged (e.g., weaved, knitted, etc.) is not compressive or is less compressive than would be required to prevent the male external genitalia from entering the support pouch.

The anterior-projecting contour of support pouch 126 is depicted in FIG. 1C. Note that the contour is depicted for pedagogical purposes; the pouch does not have a smooth or defined contour as shown. In actuality, the ample amount of fabric is "loose" and the pouch has minimal volume or 3-d form until garment 100 is in use by a male wearer.

FIG. 1D depicts a simplified partial representation of a male 134 wearing radiation treatment garment 100. As depicted in FIG. 1D, external male genitalia 136 protrudes through opening (not depicted) in the compression fabric and into support pouch 126.

Using too little fabric to form support pouch 126 will result in a pouch that presents a resistance to receiving the external male genitalia. This is undesirable since the genitalia will then not be positioned sufficiently anterior to the body to best avoid the radiation treatment field. Using what might otherwise appear to be an excessive amount of fabric to form support pouch 126 will not significantly impact the ability of pouch to provide support. This is because a narrowing of support pouch 126 at the inferior edge thereof tends to support the male external genitalia in the pouch at a position that is superior to the natural gravity-induced position, regardless of the amount of fabric present. In any case, an appropriate amount of fabric appropriately attached to front 101 of garment 100 will form a support pouch that is capable of positioning the external male genitalia anterior (forward) and superior (up) relative to the peritoneal region. The material used for support pouch 126 must not scatter the radiation treatment beam or add bolus effect. It is within the capabilities of those skilled in the art, after reading the present disclosure, to select a suitable fabric in an appropriate amount to form support pouch 126.

In some embodiments, at least upper edge 128 of support pouch 126 is removably attached to the shorts. For example, a strip of hook-and-loop fastener can be attached to upper edge 128 of the support pouch and a complementary strip of hook-and-loop fastener can be disposed on front 101 of garment 100. Or the garment can comprise a "hook-compatible fabric" (i.e., VELCRO® receptive), such that the strip of hook-and-loop fastener will simply "stick" to the fabric. Such fabric is commercially available from Darlington Fabrics of Westerly, R.I., and others. This capability enables a wearer to "drop" upper edge 128 of support pouch 126 to urinate, for example. Furthermore, it provides some adjustability to the amount of "lift" provided by support pouch 126.

Referring again to FIGS. 1A and 1B, loops 130 are attached to exterior of garment 100 beneath inferior edge 116 of lateral window portion 114. Loops 130 are used to aid a wearer in donning garment 100 by, for example, slipping a finger through each loop and pulling the garment "up." Loops 130 are provided since it was found that as a consequence of the intended snug fit of garment 100, window 106 is prone to tearing along the interface of the window and the compression fabric, such as at region 118. Since loops 130 are disposed on garment 100 below window 106, there is far less stress at the window/compression-fabric interface when pulling "up" at the loops.

To further decrease a tendency for window 106 to tear, in some embodiments, the interface is curved or rounded at regions 118. This avoids a geometric discontinuity—a sharp corner in this case—that would otherwise result if lateral window portion 114 and anterior window portion 108 met at a right angle (90 degrees). These discontinuities cause a local increase in the intensity of a stress field (a "stress concentrator"), such as the stress field caused when garment 100 is pulled upward at waist band 104 while the compression fabric clings tightly to the legs of the soon-to-be wearer. Window 106 is more likely to fail at region 118 when it is in the form of a sharp corner. Although the interfaces at regions 120, 122, and 124 (on both sides of garment 100) are not as problematic, in some embodiments, one more of these interfaces are curved or rounded as well.

Figure 2B:
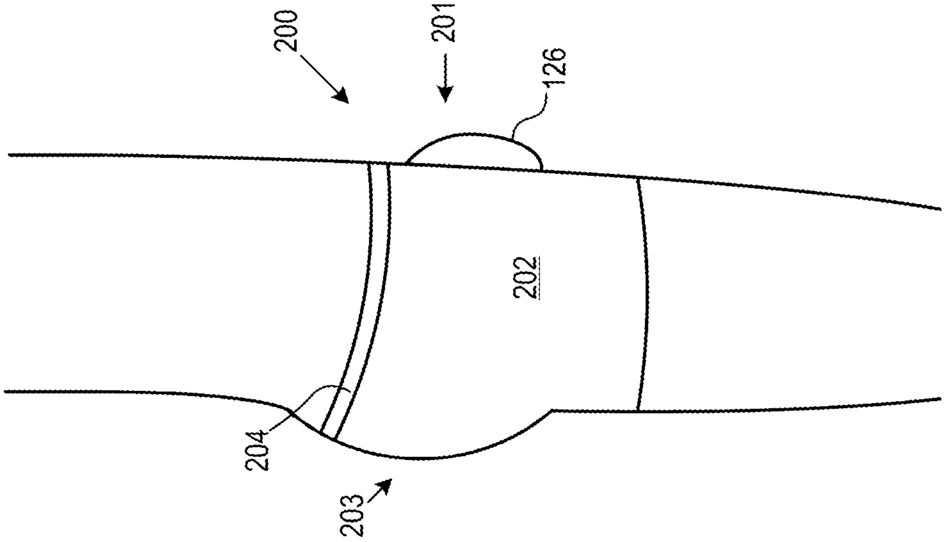
FIG. 2B depicts a side view of the radiation treatment garment of FIG. 2A.
Figure 2A:
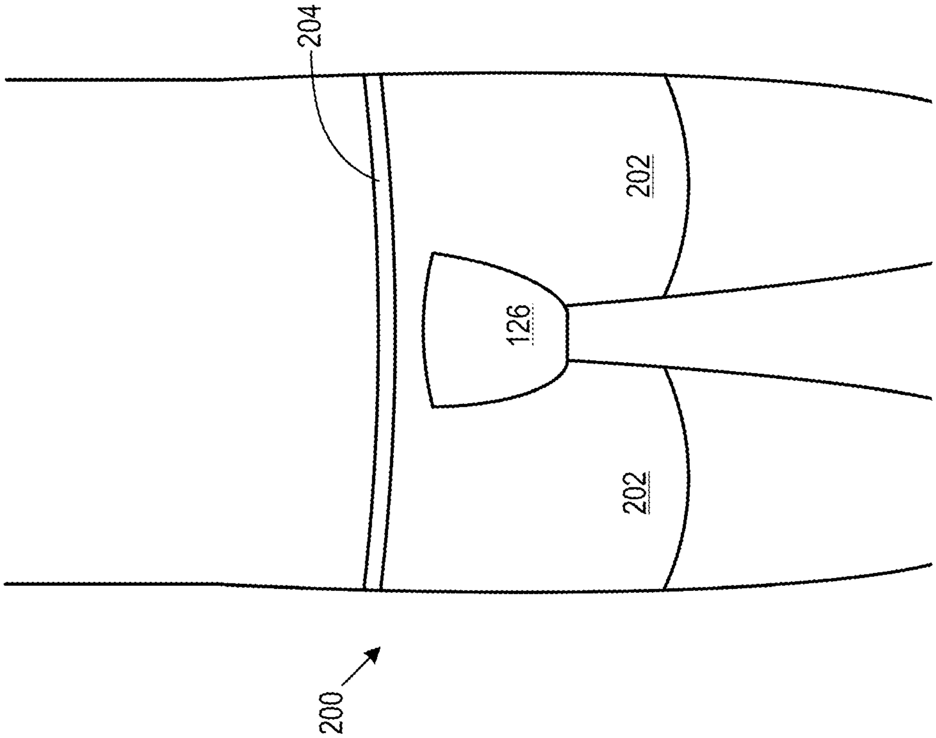
FIG. 2A depicts a front view of a second embodiment of a radiation treatment garment in accordance with the present invention.

FIGS. 2A and 2B depict respective front and side views of radiation treatment garment 200 in accordance with a second embodiment of the present invention. Like garment 100, garment 200 is in the form of a pair of "shorts," which are intended (but not restricted) for use by men.

Garment 200 includes front portion 201, leg portions 202, back portion 203, and waist band 204.

Garment 200 differs from garment 100 in that garment 200 does not include one or more "windows" like garment 100. Garment 200 is sufficiently "low cut" so that any alignment tattoos will be visible above waist band 204.

Garment 200 includes support pouch 126, which is in the same location and serves the same function as support pouch 126 of garment 100.

Figure 3B:
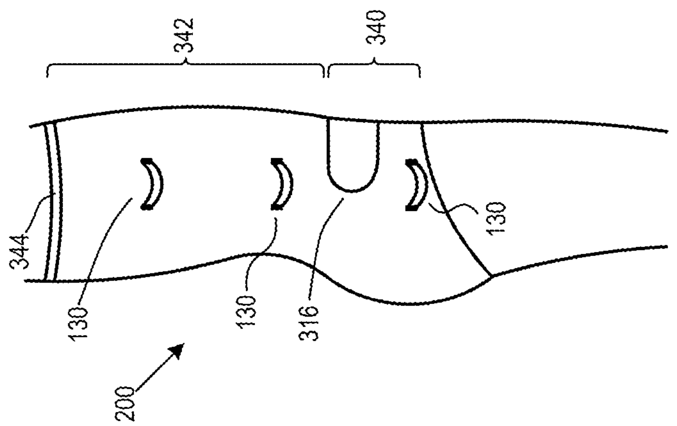
FIG. 3B depicts a side view of the radiation treatment garment of FIG. 3A.
Figure 3A:
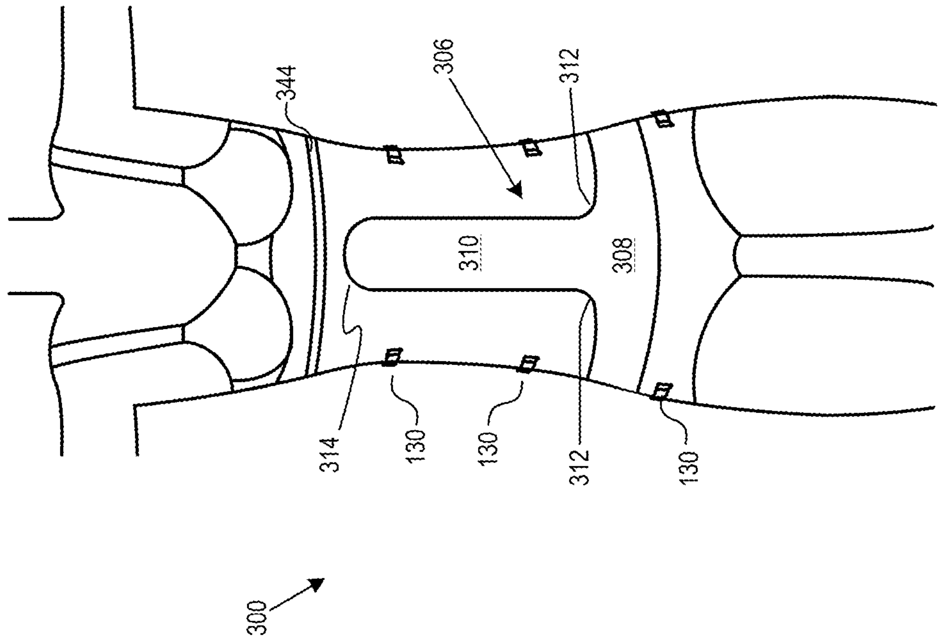
FIG. 3A depicts a front view of a third embodiment of a radiation treatment garment in accordance with the present invention.

FIGS. 3A and 3B depict radiation treatment garment 300 in accordance with a third illustrative embodiment of the present invention. Garment 300 is in the form of a shape-wear girdle. The brassiere depicted in FIG. 3A is not part of garment 300.

Garment 300 includes bottom region 340, torso region 342, and chest band 344.

Most of bottom region 340 and torso region 342 comprise a compression fabric like that used in conjunction with garments 100 and 200. The compression fabric selected, which is the primary constituent of garment 300, must not scatter or otherwise substantially attenuate the radiation treatment beam or add bolus effect.

Chest band 344 encircles the top opening of garment 300 near the superior edge thereof. The function of chest band 344 is analogous to the function of waistband 104 of garment 100; it is intended to keep the garment snug to the wearer. Chest band 344 comprises an elastic material, such as a fabric comprising 90% nylon and 10% spandex, as is available from Stretchline (UK). Other compositions and materials may suitably be used. In some alternative embodiments, a discrete chest band is not provided since the compression fabric from which garment 300 is made is suitable for keeping it snug to the wearer.

Garment 300 also includes a window 306, which is similar in construction to window 106 in that it is not simply an "opening" in the garment. That is, window comprises a transparent material. Also, window 306 has the same function as window 106 of garment 100 (e.g., viewing alignment tattoos, etc.).

Window 306 comprises window portion 310 and window portion 308. Window portion 310, which is located in torso region 342, extends downward along the mid-line of the torso portion from a point proximal to chest band 344 to about the level of the umbilicus. Window portion 310 has a width in a range of about 5 centimeters to 10 centimeters.

Window portion 308, which is disposed in bottom region 340, extends laterally across the front of garment 300, terminating at approximately the vertical mid-line at the right and left sides of the garment. Guidelines for the relative location of window portion 308 with respect to a wearer are the same as previously provided for window 106 of garment 100. In garment 300, window 306 is continuous; that is, window portion 310 and window portion 308 are not segregated by fabric from one another.

Like the windows in garment 100, window 306 comprises a clear/visually-transparent material that is free of metals or other constituents that will scatter or substantially attenuate the radiation treatment beam or cause bolus effect. The aforementioned clear thermoplastic material, Clear-Fit TPU brand thermoplastic polyurethane, commercially available from Fulflex, Inc. of Brattleboro, Vt., is suitable for use.

Loops 130 are attached to the exterior of garment 300 to aid a wearer in donning the garment. In some embodiments, loop 130 is disposed on each side of garment 300 in bottom region 340. In some further embodiments, additional loops 130 are provided in torso region 342.

As discussed in conjunction with garment 100, to decrease any tendency for the window to separate from the compression fabric along the interface thereof, sharp edges are avoided along the interface. For example, in garment 300, the interface is rounded at regions 312, 314, and 316.

As previously indicated, the snug fit provided by garment 300 controls, or otherwise smoothes the skin/tissue to reduce or prevent folds, etc., which can cause a variety of problems, such as the non-homogenous distribution of radiation, and dry and moist desquamation. Window 306 enables garment 300 to be used during radiation planning sessions as well as radiation treatment sessions. And bottom region 340 provides "cover" so that a patient undergoing treatment need not be naked.

Figure 4B:
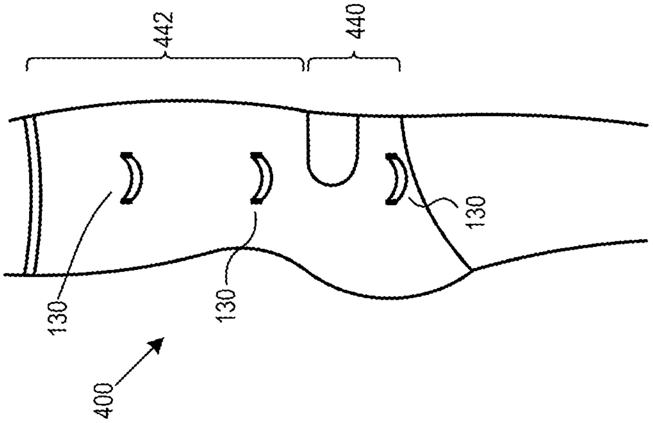
FIG. 4B depicts a side view of the radiation treatment garment of FIG. 4A.
Figure 4A:
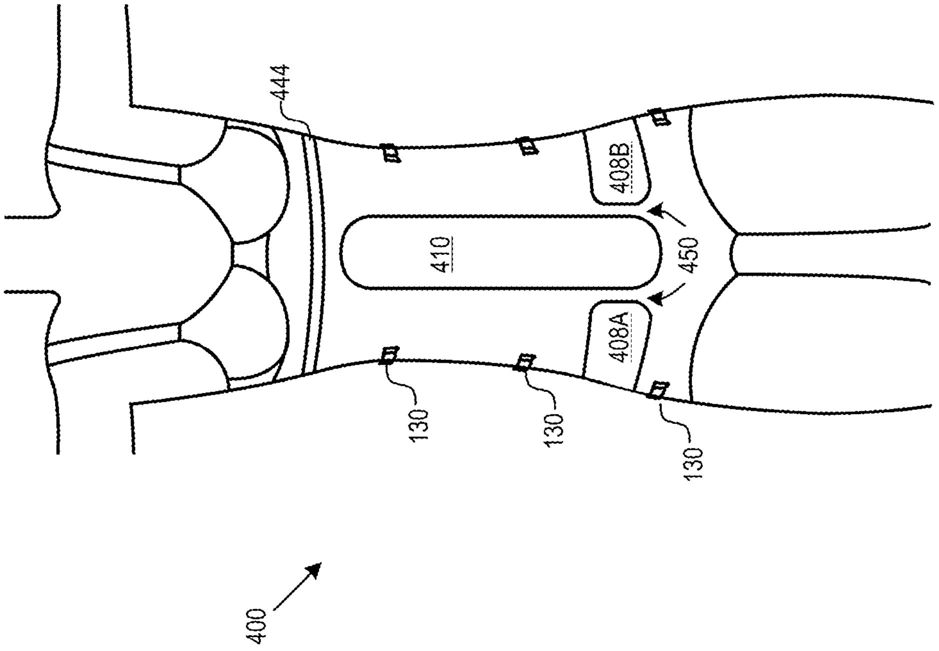
FIG. 4A depicts a front view of a fourth embodiment of a radiation treatment garment in accordance the present invention.

FIGS. 4A and 4B depict radiation treatment garment 400 in accordance with a fourth illustrative embodiment of the present invention. Garment 400, like garment 300, is in the form of a shape-wear girdle. The brassiere depicted in FIG. 4A is not part of garment 400.

Garment 400 includes bottom region 440, torso region 442, and chest band 444. Like radiation treatment garments 100, 200, and 300 previously discussed, garment 400 predominantly comprises a compression fabric. Chest band 444 is of the same construction and purpose as chest band 344 of garment 300.

Garment 400 includes three discrete windows: window 410 in torso region 442 and windows 408A and 408B in bottom region 440. Window 410 has a width in a range of about 5 centimeters to 10 centimeters. By segregating the windows, torso region 442 and bottom region 440 can be made "continuous," such as at regions 450. This reinforces the window/compression fabric interfaces (compare, for example, to regions 312 in garment 300) so that they are better able to withstand the stresses experienced as a patient dons garment 400. Garment 400 includes loops 130, for the reasons previously discussed, in both bottom region 440 and torso region 442, or only in bottom region 440.

Figure 5:
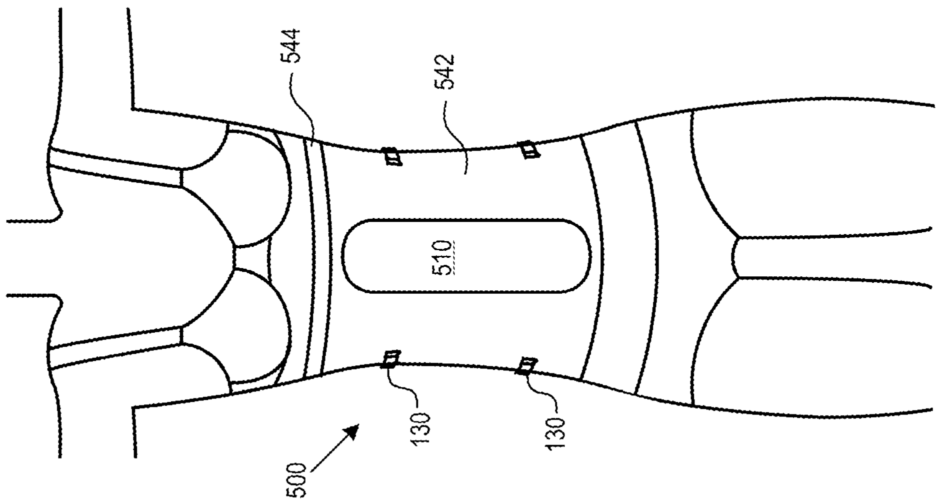
FIG. 5 depicts a front view of a fifth embodiment of a radiation treatment garment in accordance with the present invention.

FIG. 5 depicts radiation treatment garment 500 in accordance with a fifth illustrative embodiment of the present invention. Garment 500, like garments 300 and 400, is in the form of a shape-wear girdle. Unlike garments 300 and 400, garment 500 does not include a "bottom" region. For such an embodiment, the patient can wear a pair of panties, etc. for radiation planning and treatment sessions. The brassiere depicted in FIG. 5 is not part of garment 500.

Garment 500 includes a body portion 542 and chest band 544. Like radiation treatment garments previously discussed, garment 500 predominantly comprises a compression fabric. Chest band 544 is of the same construction and purpose as chest bands 344 and 444 of respective radiation treatment garments 300 and 400.

Garment 500 includes a single window 510, located along the vertical mid-line of body portion 542. The window extends downward from a point proximal to chest band 544 to about the level of the umbilicus. Window 510 has a width in a range of about 5 centimeters to 10 centimeters.

Garment 500 includes loops 130 along body portion 542 for aiding a patient to don the garment.

Although not depicted, in some embodiments, the back of torso region 342 of radiation treatment garment 300, the back of torso region 442 of radiation treatment garment 400, and the back of body portion 542 of garment 500 have a vertical "split" running down the vertical mid-line thereof. This facilitates donning these garments. A closure, such as hook-and-loop fastener (i.e., VELCRO®) is disposed at the split so that the garments can be closed with the assistance of radiation treatment personnel.

Girdle embodiments 300, 400, and 500 can suitably be adapted for use by men. For example, as appropriate, these embodiments can be modified to include support pouch 126. And, of course, shorts embodiments 100 and 200 can be suitably adapted for use by women. For example, support pouch 126 can be omitted.

As previously disclosed, radiation treatment garments in accordance with the present invention are intended to control or smooth the skin/tissue to substantially reduce or prevent folds, etc., that can cause a variety of problems. As a consequence, the radiation treatment garments disclosed herein are intended to fit quite snugly. For this reason, the windows shown in garments 100, 300, 400, and 500 cannot simply be "openings;" that is, they must be covered by (visually-transparent) material. If the windows were simply openings, then the skin, particularly in the case of an overweight/obese person, would tend to protrude from these openings, causing the problems noted above.

It is to be understood that the disclosure teaches just one example of the illustrative embodiment and that many variations of the invention can easily be devised by those skilled in the art after reading this disclosure and that the scope of the present invention is to be determined by the following claims.

What is claimed is:

1. A radiation treatment garment physically configured as a pair of shorts, wherein the shorts are formed, in major part, from a compression fabric, and wherein the shorts comprise:

a back portion for covering a wearer's buttocks;

leg portions having leg openings; and a front portion, wherein the back portion, leg portions and front portion are attached to form the shorts, the shorts further comprising:

a window defined in the front portion of the shorts, wherein the window comprises a clear, visually-transparent material and further wherein an anterior portion of the window extends laterally across the front portion of the shorts; and a support pouch, wherein the support pouch covers an opening in the front portion of the shorts configured to be directly proximal to a male wearer's external genitalia, wherein the support pouch comprises a non-compression fabric present in a quantity suitable for defining a volume that is sufficient for receiving the external genitalia through the opening without resistance, and wherein the support pouch is configured to support the external genitalia in a position that is anterior and superior to a natural gravity-induced position.

2. The radiation treatment garment of claim 1 further comprising a waist band, wherein the waist band defines a superior edge of the shorts.

3. The radiation treatment garment of claim 2 wherein the clear, visually-transparent material that forms the window is suitable for being penetrated by a device for creating a permanent alignment mark on a skin of the wearer beneath the window.

4. The radiation treatment garment of claim 1 wherein the window further comprises a right lateral portion disposed on a right side of the shorts and a left lateral portion disposed on a left side of the shorts, wherein the right lateral portion and the left lateral portion of the window extend inferiorly to the anterior portion of the window.

5. The radiation treatment garment of claim 4 wherein:

(a) a first intersection of the anterior portion of the window with the right lateral portion, at an interface with the compression fabric, is rounded; and (b) a second intersection of the anterior portion of the window with the left lateral portion, at an interface with the compression fabric, is rounded.

6. The radiation treatment garment of claim 1 further comprising a waist band defining a superior edge of the shorts.

7. The radiation treatment garment of claim 6 further comprising at least two loops of material attached thereto, wherein each loop is configured to receive a finger of the wearer and is disposed inferior to the window.

8. The radiation treatment garment of claim 1 wherein the window is positioned to provide a view of:

(a) a lower abdomen of the wearer; and (b) a view of the wearer's left hip and right hip proximal to the iliac crest.

9. The radiation treatment garment of claim 1 further comprising at least two loops of material, wherein one of the two loops is disposed on the left side of the front portion of the shorts and a second of the two loops is disposed on the right side of the front portion of the shorts, wherein each loop is configured to receive a finger of the wearer and wherein all of the at least two loops disposed on respective left and right sides of the shorts are inferior to the window.

10. The radiation treatment garment of claim 1 and further wherein the clear, visually transparent material is a clear thermoplastic that is free of constituents that will scatter or attenuate a radiation beam.

11. The radiation treatment garment of claim 1 and further wherein the clear, visually transparent material is a clear thermoplastic polyurethane.

12. A radiation treatment garment physically configured as a pair of shorts, formed, in major part, from a compression fabric, the shorts having a front portion, a back portion, and leg portions, and wherein the shorts comprise:

a window, wherein the window comprises a clear, visually-transparent material, wherein an anterior portion of the window extends laterally across the front portion of the shorts; and a support pouch, wherein the support pouch covers an opening in the front portion of the shorts directly proximal to a male wearer's external genitalia, wherein the support pouch comprises a non-compression fabric present in a quantity suitable for defining a volume that is sufficient for receiving the external genitalia through the opening without resistance, and wherein the support pouch is configured to support the external genitalia in a position that is anterior and superior to a natural gravity-induced position.

13. The radiation treatment garment of claim 12 wherein the window further comprises a right lateral portion disposed on a right side of the shorts and a left lateral portion disposed on a left side of the shorts, wherein the right lateral portion and the left lateral portion of the window extend inferiorly to the anterior portion of the window.

14. The radiation treatment garment of claim 13 further comprising at least two loops of material attached thereto, wherein each loop is configured to receive a finger of the wearer and is disposed inferior to the window.

15. The radiation treatment garment of claim 12 wherein the window is positioned to provide a view of:

(a) a lower abdomen of the wearer; and (b) a view of the wearer's left hip and right hip proximal to the iliac crest.

16. The radiation treatment garment of claim 12 further comprising at least two loops of material attached thereto, wherein each loop is configured to receive a finger of the wearer and is disposed inferior to the window.

17. A radiation treatment garment physically configured as a pair of shorts, wherein the shorts are formed, in major part, from a compression fabric, and wherein the shorts comprise:

a back portion for covering a wearer's buttocks;

leg portions having leg openings; and a front portion, wherein the back portion, leg portions and front portion are attached to form the shorts, the shorts further comprising:

a window, wherein the window comprises a clear, visually-transparent material, wherein an anterior portion of the window extends laterally across the front portion of the shorts.

18. The radiation treatment garment of claim 17 wherein an inferior edge of the anterior portion of the window is configured to be no more than about 5 centimeters superior to the wearer's pubic symphysis.

19. The radiation treatment garment of claim 17 and further wherein the visually transparent material is a clear thermoplastic that is free of constituents that will scatter or attenuate a radiation beam.

20. The radiation treatment garment of claim 17 and further wherein the visually transparent material is a clear thermoplastic polyurethane.

21. A radiation treatment garment physically configured as a pair of shorts having:

a waist band at a superior edge thereof, a front portion including a support pouch for receiving male external genitalia of the wearer of the shorts, a back portion for covering the wearer's buttocks, and leg portions having leg openings, and wherein the garment further comprises:

as a primary constituent, a compression fabric for supplying compression to portions of the wearer's body covered thereby, wherein the back portion, at least part of the leg portions, and at least part of the front portion comprise the compression fabric;

as a first minor constituent, a non-compression fabric that covers an opening formed in the front portion, wherein the non-compression fabric is present in a sufficient quantity and is attached to the front portion in such a way as to define the support pouch and enable the support pouch to support the external genitalia of a male wearer in a position that is anterior and superior to a natural gravity-induced position, wherein the external genitalia protrudes though the opening into the support pouch; and as a second minor constituent, a clear, visually transparent material that defines at least one window in the front portion of the garment, wherein the window is adjacent to and below the waist band and at least a portion of the window is above the support pouch.

22. The radiation treatment garment of claim 21 further comprising at least two loops of material attached thereto, wherein each loop is configured to receive a finger of the wearer and is disposed inferior to the window.

23. The radiation treatment garment of claim 21 and further wherein the second minor constituent is a clear thermoplastic that is free of constituents that will scatter or attenuate a radiation beam.

24. The radiation treatment garment of claim 21 and further wherein the second minor constituent is a clear thermoplastic polyurethane.

* * * * *